United States Patent [19]

Nakayama et al.

[11] Patent Number: 4,507,500

[45] Date of Patent: Mar. 26, 1985

[54] PROCESS FOR PRODUCING 2-MERCAPTOETHYLAMINE HYDROHALIDES

[75] Inventors: Shigenobu Nakayama, Kamakura; Eiichi Noda, Fujisawa; Yoshiaki Noguchi, Yokohama; Isamu Yamamoto, Zushi; Noboru Kawasaki, Kamakura, all of Japan

[73] Assignee: Mitsui Toatsu Chemicals, Inc., Tokyo, Japan

[21] Appl. No.: 281,091

[22] Filed: Jul. 7, 1981

[30] Foreign Application Priority Data

Jul. 15, 1980 [JP] Japan ................................ 55-95642

[51] Int. Cl.[3] .......................................... C07C 149/24
[52] U.S. Cl. .................... 564/340; 564/341; 564/487; 564/500
[58] Field of Search ............... 564/340, 341, 487, 500

[56] References Cited

PUBLICATIONS

Pavalova et al., "Chemical Abstracts", vol. 63, p. 18068a, (1965).
Clapp et al., "Journal Org. Chem.", vol. 26, pp. 1666–1668, (1961).
Gaul et al., "Journal Org. Chem.", vol. 25, pp. 869–871, (1960).
Johnston et al., "Journal Org. Chem.", vol. 29, pp. 2442–2444, (1964).

*Primary Examiner*—Robert V. Hines
*Attorney, Agent, or Firm*—Fisher, Christen and Sabol

[57] ABSTRACT

A process for producing 2-mercaptoethylamine hydrohalides of the general formula

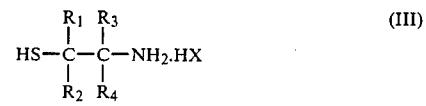

wherein $R_1$, $R_2$, $R_3$ and $R_4$ are identical or different, and each represents a hydrogen atom, a lower alkyl group, a hydroxy-substituted lower alkyl group or a phenyl group, and X represents a halogen atom, which comprises reacting a 2-mercaptothiazoline of the general formula

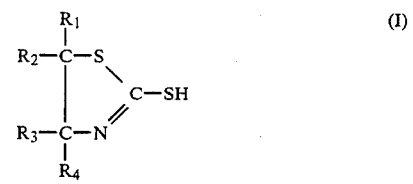

wherein $R_1$, $R_2$, $R_3$ and $R_4$ are as defined above, with a 2-halogenoethylamine hydrohalide of the general formula

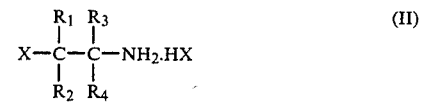

wherein $R_1$, $R_2$, $R_3$, $R_4$ and X are as defined above, in the presence of water.

18 Claims, No Drawings

PROCESS FOR PRODUCING 2-MERCAPTOETHYLAMINE HYDROHALIDES

BACKGROUND OF THE INVENTION

1. Field of the Invention

This invention relates to a process for producing 2-mercaptoethylamine hydrohalides. More specifically, it pertains to a process for producing 2-mercaptoethylamine hydrohalides which comprises reacting 2-mercaptothiazolines with 2-halogenoethylamine hydrohalides in the presence of water.

2. Description of the Prior Art

The 2-mercaptoethylamine hydrohalides are very useful compounds as various materials for producing medicines, intermediates for production of hair-dressing cosmetics and also as radiation protecting substances.

Among known processes for production of 2-mercaptoethylamine hydrohalides are:

(A) A process which comprises the action of an alkylenimine on a large excess of an alcohol solution of hydrogen sulfide under cooling [Ann., 566, 210 (1950); J. Chem. Soc., 1944, 5).

(B) A process which comprises reacting an alkylenimine with a dialkyl ketone, and thereafter treating the reaction product with hydrogen sulfide and then with a hydrohalic acid [Bull. Soc. Chim. Fr., 1964, 2493; Ann. 566, 210 (1950); Japanese Patent Publication No. 29444/1975; and Japanese Patent Publication No. 41569/1979].

(C) A process which comprises reacting oxazoline with hydrogen sulfide and hydrolyzing the product in an aqueous solution of hydrochloric acid (Japanese Laid-Open Patent Publication No. 128509/1979; U.S. Pat. No. 4,086,274).

(D) A process which comprises reacting an aminoalkyl sulfuric acid ester with hydrogen sulfide and an alkali polysulfide prepared from an alkali hydrosulfide and sulfur, and thereafter treating the product with hydrochloric acid (Japanese Laid-Open Patent Publication No. 11506/1980).

(E) A process which comprises hydrolyzing 2-mercaptothiazoline using hydrochloric acid or hydrobromic acid [J. Org. Chem., 25, 869 (1960); Ber., 31, 2832 (1898)].

These processes, however, have the following problems when they are used industrially.

Processes (A) to (C) require the use of alkylenimines which are carcinogenic, or poisonous hydrogen sulfide gas as starting materials. Process (D) is better than processes (A) to (C) in that it does not involve handling of hydrogen sulfide gas itself but allows it to be generated in the reaction solution. However, since the reaction is carried out under alkaline conditions, bis(2-aminoethyl)sulfides and bis(2-aminoethyl)disulfides (oxidized dimers of 2-mercaptoethylamines; trivially called cystamines), which are difficult to separate from 2-mercaptoethylamines, are formed as by-products to reduce the purity and yield of the desired 2-mercaptoethylamines. According to process (E), poisonous hydrogen sulfide gas is formed as a by-product in an amount equivalent to the amount of the starting material reacted.

It is an object of this invention to provide a process for producing highly pure 2-mercaptoethylamine hydrohalides more safely and at lower costs.

SUMMARY OF THE INVENTION

According to this invention, there is provided a process for producing 2-mercaptoethylamine hydrohalides of the general formula

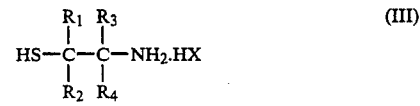

wherein $R_1$, $R_2$, $R_3$ and $R_4$ are identical or different, and each represents a hydrogen atom, a lower alkyl group, a hydroxy-substituted lower alkyl group or a phenyl group, and X represents a halogen atom, which comprises reacting a 2-mercaptothiazoline of the general formula

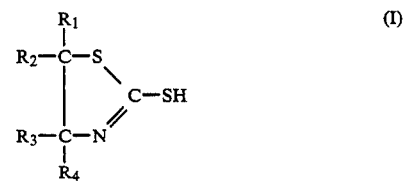

wherein $R_1$, $R_2$, $R_3$ and $R_4$ are as defined above, with a 2-halogenoethylamine hydrohalide of the general formula

wherein $R_1$, $R_2$, $R_3$, $R_4$ and X are as defined above, in the presence of water.

DETAILED DESCRIPTION OF THE PRESENT INVENTION

The present invention embraces a process for producing 2-mercaptoethylamine hydrohalides by the one-step reaction shown by scheme (1) below, and a process for producing 2-mercaptoethylamine hydrohalides by the two-step reactions shown by schemes (2) and (3) below, i.e. through S,S'-bis(2-aminoethyl)dithiocarbonate derivatives of the formula

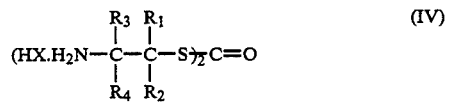

wherein all symbols are as defined above, as an intermediate.

Scheme (1)

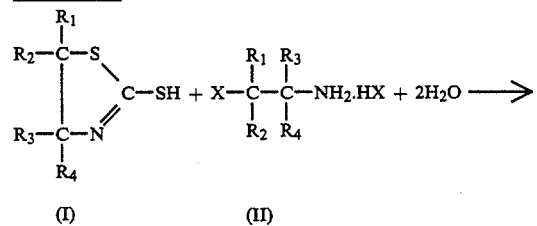

-continued

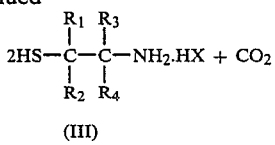
(III)

Scheme (2)

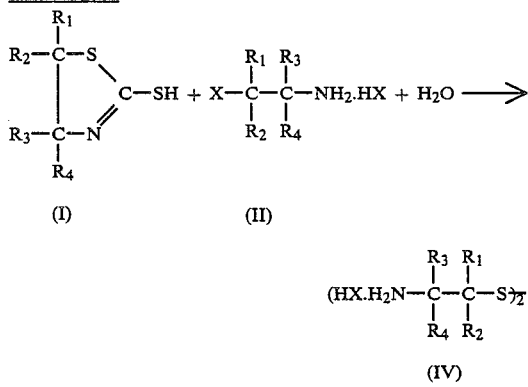

Scheme (3)

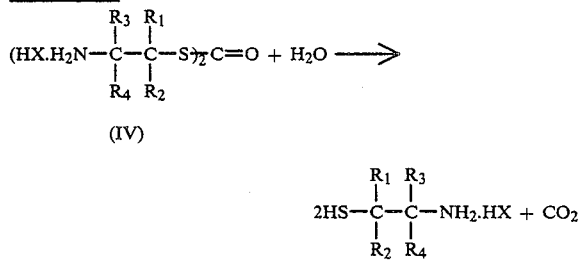

The process of this invention can give 2-mercaptoethylamines very safely because the starting materials are of low toxicity and the reactions involved do not substantially yield poisonous gases. Furthermore, since the reactions in the process of this invention are carried out substantially under acidic conditions, by-products such as bis(2-aminoethyl)sulfides and bis(2-aminoethyl)disulfides are not formed and very pure 2-mercaptoethylamines can be obtained.

The 2-mercaptothiazolines of general formula (I) used in the process of this invention can be easily produced by known methods, for example, (1) a method which comprises reacting a sulfuric acid ester of a monoethanolamine with relatively easily handleable carbon disulfide in the presence of an alkali (J. Chem. Soc., 1976, page 1367), (2) a method which comprises reacting a monoethanolamine with twice its amount of carbon disulfide in the presence of an alkali [Chemical Abstracts, Vol. 53, 9045e (1959)], or (3) a method which comprises reacting a 2-halogenoethylamine with carbon disulfide in the presence of an alkali (U.S. Pat. No. 2,251,459). Specific examples of the compounds of general formula (I) include 2-mercaptothiazoline, 4-phenyl-2-mercaptothiazoline, 4,5-diphenyl-2-mercaptothiazoline, 4-methyl-2-mercaptothiazoline, 4,4-dimethyl-2-mercaptothiazoline, 4,4-bis(hydroxymethyl)-2-mercaptothiazoline, 4-butyl-5-phenyl-2-mercaptothiazoline, 5,5-dimethyl-2-mercaptothiazoline, 5-ethyl-2-mercaptothiazoline, 4,5-dimethyl-2-mercaptothiazoline, 4,4,5-trimethyl-2-mercaptothiazoline, 4,4,5,5-tetramethyl-2-mercaptothiazoline, 4,5-bis(hydroxymethyl)-2-mercaptothiazoline, 4-phenyl-5-butyl-2-mercaptothiazoline, 4-propyl-2-mercaptothiazoline, 4-ethyl-2-mercaptothiazoline, 5-propyl-2-mercaptothiazoline, 4-methyl-5-phenyl-2-mercaptothiazoline, and 5-methyl-2-mercaptothiazoline.

Specific examples of the 2-halogenoethylamine hydrohalides of general formula (II) used in the process of this invention include hydrohalides of 2-halogenoethylamines, 1-phenyl-2-halogenoethylamines, 1,2-diphenyl-2-halogenoethylamines, 1-methyl-2-halogenoethylamines, 1,1-dimethyl-2-halogenoethylamines, 1,1-bis(hydroxymethyl)-2-halogenoethylamines, 1-butyl-2-phenyl-2-halogenoethylamines, 2,2-dimethyl-2-halogenoethylamines, 2-ethyl-2-halogenoethylamines, 1,2-dimethyl-2-halogenoethylamines, 1,1,2-trimethyl-2-halogenoethylamines, 1,1,2,2-tetramethyl-2-halogenoethylamines, 1,2-bis(hydroxymethyl)-2-halogenoethylamines, 1-phenyl-2-butyl-2-halogenoethylamines, 1-propyl-2-halogenoethylamines, 1-ethyl-2-halogenoethylamines, 2-propyl-2-halogenoethylamines, 1-methyl-2-phenyl-2-halogenoethylamines and 2-methyl-2-halogenoethylamines. In these compounds, the halogen is preferably chlorine, bromine or iodine. These compounds of formula (II) can be easily produced by known methods, for example, (1) a method which comprises the action of a hydrohalic acid on a monoethanolamine, (2) a method which comprises the action of thionyl chloride on a monoethanolamine [Ger. Offen. No. 2,701,215 (1978)].

In the process of the invention, the amounts of the 2-mercaptothiazoline and the 2-halogenoethylamine hydrohalide used may be equimolar in theory, but amounts outside this range do not substantially affect the reaction. In order to inhibit side reactions, however, it is especially preferable to use 1.02 to 1.20 moles of the 2-mercaptothiazoline per mole of the 2-halogenoethylamine hydrohalide.

The amount of water may exceed the theoretical amount because the process of the invention proceeds in accordance with the reaction scheme (1), or reaction schemes (2) and (3). The amount of water used, however, determines the type of the reaction. If the amount of water is large, the one-step reaction according to scheme (1) proceeds, and if it is small, the reaction according to scheme (3) becomes very slow and therefore the two-step reactions according to schemes (2) and (3) proceed. In the process according to scheme (1), the amount of water is generally at least 20 moles, preferably at least 22 moles, per mole of the compound of general formula (I) or (II). On the other hand, when the process is carried out according to reaction schemes (2) and (3), it is desired to perform the reaction according to scheme (2) selectively. Thus, the reaction according to scheme (2) is carried out by using water in an amount of less than 20 moles, preferably 1.5 to 15 moles, per mole of the starting material of general formula (I) or (II), and then the reaction according to scheme (3) is carried out in the presence of an additional amount of water supplied as required.

The end point of the reaction according to scheme (2) is judged by ascertaining the disappearance of the material of general formula (II) or the formation of the intermediate of general formula (IV) using an ordinary analyzing means such as gas chromatography, liquid chromatography or thin-layer chromatography. The product of the reaction (2) is the S,S'-bis(2-aminoethyl)dithiocarbonate derivative of general formula (IV) although, strictly, it contains small amounts of the unreacted 2- mercaptothiazoline and the 2-mercaptoethylamine hydrohalide as a final product.

The process of this invention can substantially be performed in an aqueous solution. In order to increase the rate of the reaction, it may also be carried out in an aqueous solution of a hydrohalic acid.

The process of the invention does not substantially require a solvent other than water. But depending upon the material used, an organic solvent inert to the reaction may be used as required in order to increase the solubility of the material. The presence of such a solvent in the reaction system does not at all affect the reaction. The organic solvent inert to the reaction is a solvent which does not react with the starting materials, the product, etc. Both water-miscible and water-immiscible inert organic solvents can be used. Specific examples include aliphatic hydrocarbons such as hexane and heptane, aromatic hydrocarbons such as benzene, toluene and xylene, aliphatic alcohols such as ethanol, propanol and butanol, alicyclic alcohols such as cyclohexanol, aliphatic ethers such as butyl ether and diglyme, alicyclic ethers such as tetrahydrofuran and dioxane, sulfur-containing compounds such as dimethyl sulfoxide and sulfolane, and nitrogen-containing compounds such as dimethyl formamide. Hexane, heptane, toluene, xylene, propanol, butanol and dimethyl formamide are preferred.

The reactions (1), (2) and (3) in the process of this invention may be carried out at any desired temperature. From the viewpoint of the rate of reaction, the reaction temperature is generally 20° C. to 200° C., preferably 50° C. to 150° C. The two reactions (2) and (3) may be carried out at the same temperature, or the temperature may be changed during the reaction.

After the reaction, water and the organic solvent (when used) are distilled off under reduced pressure, and the residue is concentrated to dryness. Thus, the 2-mercaptoethylamine hydrohalide can be obtained in a nearly quantitative yield as highly pure crystals.

The 2-mercaptoethylamine hydrohalides obtained by the present invention generally have a high purity. Those obtained by the two-step process in accordance with reaction schemes (2) and (3) have a higher purity. 2-Mercaptoethylamine hydrohalides having a still higher purity can be obtained by separating the compound of general formula (IV), i.e. S,S'-bis(2-aminoethyl)dithiocarbonate, after the reaction according to scheme (2), purifying it, and then subjecting the purified compound of formula (IV) to the reaction of scheme (3).

The following Examples illustrate the present invention more specifically.

EXAMPLE 1

A 100 ml four-necked flask equipped with a stirrer, a thermometer and a reflux condenser was charged with 2.98 g (0.025 mole) of 2-mercaptothioazoline, 2.90 g (0.025 mole) of 2-chloroethylamine hydrochloride and 50 g (2.78 moles) of water, and they were heated at the refluxing temperature (98° to 100° C.) for 50 hours with stirring. After the reaction, water was distilled off under reduced pressure, and the residue was concentrated to dryness to give white crystals. Recrystallization from ethanol gave 5.12 g of 2-mercaptoethylamine hydrochloride having a melting point of 70.5° to 72° C. The results of its elemental analysis for $C_2H_8NSCl$ were as follows:

|  | C | H | N | S | Cl |
|---|---|---|---|---|---|
| Calculated (%): | 21.14 | 7.10 | 12.33 | 28.22 | 31.21 |
| Found (%): | 20.99 | 7.00 | 12.35 | 28.11 | 31.45 |

The mother liquor resulting from the recrystallization was concentrated to dryness, and the concentrated product was subjected to $^1$H-NMR. It was identified as 2-mercaptoethylamine hydrochloride containing small amounts of the starting materials. Analysis of the product by thin-layer chromatography (TLC for short) gave a fairly clear spot of monoethanolamine.

EXAMPLE 2

The same reactor as described in Example 1 was charged with 18.7 g (0.157 mole) of 2-mercaptothiazoline, 17.4 g (0.150 mole) of 2-chloroethylamine hydrochloride and 15 g (0.83 mole) of water, and they were heated at 95° to 100° C. Twenty hours later, the reaction mixture was analyzed by TLC. It was found to consist of S,S'-bis(2-aminoethyl)dithiocarbonate as a main component with the 2-chloroethylamine hydrochloride disappearing almost completely. Water (40 g; 2.22 moles) was added to the reaction mixture, and subsequently, the mixture was heated under reflux (98° to 100° C.) for 30 hours with stirring. After the reaction, the reaction mixture was concentrated to dryness under reduced pressure to give 34.5 g of white crystals. As a result of iodometric analysis, these crystals were found to have a purity of 98.2% as 2-mercaptoethylamine hydrochloride. TLC of these crystals scarcely showed a spot ascribable to monoethanolamine or the starting materials.

EXAMPLE 3

The same reactor as described in Example 1 was charged with 3.10 g (0.026 mole) of 2-mercaptothiazoline, 2.90 g (0.025 mole) of 2-chloroethylamine hydrochloride and 50 ml (60 g; 2.1 moles as water) of conc. hydrochloric acid, and they were heated at the refluxing temperature (105° to 108° C.) for 20 hours with stirring. After the reaction, the hydrochloric acid was distilled off under reduced pressure, and the residue was concentrated to dryness to give white crystals. Recrystallization from ethanol gave 5.23 g of 2-mercaptoethylamine hydrochloride having a melting point of 71.5° to 72° C. The mother liquor resulting from the recrystallization was concentrated to dryness, and the concentrated product was subjected to $^1$H-NMR. It was identified as 2-mercaptoethylamine hydrochloride containing small amounts of the starting materials.

EXAMPLE 4

The same reactor as described in Example 1 was charged with 18.7 g (0.157 mole) of 2-mercaptothiazoline, 17.4 g (0.150 mole) of 2-chloroethylamine hydrochloride and 15 g (0.67 mole as water) of 20% hydrochloric acid, and they were heated at 105° to 110° C. for 10 hours. Analysis of the reaction mixture by TLC led to the determination that the 2-chloroethylamine hydrochloride disappeared almost completely, and S.S'-bis(2-aminoethyl)dithiocarbonate formed as a main product. Then, 60 g (2.67 moles as water) of 20% hydrochloric acid was added to the reaction mixture, and the mixture was heated for 20 hours under reflux. After the reaction, the reaction mixture was worked up in the same way as in Example 3 to give 31.4 g of 2-mercaptoethylamine hydrochloride having a melting point of 71° to 72° C.

EXAMPLE 5

The same reactor as described in Example 1 was charged with 12.2 g (0.102 mole) of 2-mercaptothiazoline, 20.5 g (0.100 mole) of 2-bromoethylamine hydrobromide and 80 g (4.44 moles) of water, and they were heated under reflux (98° to 100° C.) for 20 hours. After the reaction, the reaction mixture was concentrated to dryness under reduced pressure to give 32.8 g of white crude crystals. By iodometric analysis, the crude crystals had a purity of 95.8% as 2-mercaptoethylamine hydrobromide. Recrystallization from ethanol gave 27.8 g of 2-mercaptoethylamine hydrobromide having a purity of 99.4%. The melting point of the product was 159° to 160° C. The mother liquor resulting from the recrystallization was concentrated to dryness, and the concentrated product was subjected to $^1$H-NMR. It was identified as 2-mercaptoethylamine hydrobromide containing small amounts of the starting materials. Analysis by TLC showed a spot of monoethanolamine.

EXAMPLE 6

The same reactor as described in Example 1 was charged with 18.7 g (0.157 mole) of 2-mercaptothiazoline, 30.8 g (0.150 mole) of 2-bromoethylamine hydrobromide and 35 g (1.9 moles) of water, and they were reacted at 95° to 100° C. for 10 hours. The reaction mixture was analyzed by TLC. It was found that the 2-bromoethylamine hydrobromide disappeared almost completely, and S.S'-bis(2-aminoethyl)dithiocarbonate formed as a main product. Water (60 g; 3.33 moles) was added to the reaction mixture, and the reaction was continued under reflux (98° to 100° C.) for 20 hours. After the reaction, the reaction mixture was concentrated to dryness under reduced pressure to give 48.8 g of white crystals. By iodometric analysis, the crude crystals were found to have a purity of 97.6% as 2-mercaptoethylamine hydrobromide. The crude crystals had a melting point of 157° to 159° C.

EXAMPLE 7

A glass pressure vessel was charged with 7.3 g (0.055 mole) of 5-methyl-2-mercaptothiazoline, 6.5 g (0.050 mole) of 2-chloropropylamine hydrochloride and 60 g (2.50 moles as water) of 25% hydrochloric acid, and they were heated at 130° C. and 5 kg/cm$^2$ for 20 hours with stirring. After the reaction, the hydrochloric acid was removed to give 15.9 g of a pale yellow wet cake. Recrystallization from isopropanol gave 10.8 g of white crystals having a melting point of 90° to 92° C. Iodometric analysis showed that the crystals had a purity of 98.8% as 2-mercaptopropylamine hydrochloride.

EXAMPLE 8

A glass pressure vessel was charged with 14.6 g (0.110 mole) of 5-methyl-2-mercaptothiazoline, 13.0 g (0.10 mole) of 2-chloropropylamine hydrochloride and 4 g (0.19 mole as water) of 15% hydrochloric acid, and they were heated at 100° to 110° C. Fifteen hours later, the reaction mixture was analyzed by TLC. It was found that the 2-chloropropylamine hydrochloride disappeared almost completely, and S.S'-bis(1-methyl-2-aminoethyl)dithiocarbonate formed as a main product. To the reaction mixture was further added 40 g (1.67 moles as water) of 25% hydrochloric acid, and the mixture was reacted at 130° C. and 5 kg/cm$^2$ for 20 hours. After the reaction, the reaction mixture was worked up in the same way as in Example 7 to give 22.1 g of white crystals. Iodometry showed that the crystals had a purity of 99.1% as 2-mercaptopropylamine hydrochloride. The crystals had a melting point of 91° to 92° C.

EXAMPLE 9

By the procedure of Example 5, the reaction was performed at 60° to 70° C. for 50 hours using 80 g (4.00 moles as water) of a 10% aqueous solution of hydrobromic acid instead of water. After the reaction, the reaction mixture was worked up in the same way as in Example 3 to give 27.2 g of white purified crystals. Iodometry showed that these crystals had a purity of 99.5% as 2-mercaptoethylamine hydrobromide. The crystals had a melting point of 159° to 161° C.

EXAMPLE 10

In the procedure of Example 6, 25 g (1.11 moles as water) of a 20% aqueous solution of hydrobromic acid was used in the first-step reaction instead of water, and 60 g (3.00 moles as water) of a 10% aqueous solution of hydrobromic acid was used in the second-step reaction instead of water. At 60° to 70° C., the first-step reaction was performed for 15 hours, and the second-step reaction, for 40 hours. After the reaction, the reaction product was worked up in the same way as in Example 4 to give 48.5 g of white crude crystals. By iodometric analysis, the crystals were found to have a purity of 97.3% as 2-mercaptoethylamine hydrobromide. The crystals had a melting point of 159° to 160.5° C.

EXAMPLE 11

The same reactor as described in Example 1 was charged with 6.78 g (0.025 mole) of 4,5-diphenyl-2-mercaptothiazoline, 6.70 g (0.025 mole) of 1,2-diphenyl-2-chloroethylamine hydrochloride, 10 g (0.56 mole) of water and 40 ml of dimethyl formamide. They were heated at 130° to 135° C. for 30 hours. After the reaction, water and dimethyl formamide were distilled off under reduced pressure to give 13.6 g of a viscous pale yellow liquid. By $^1$-H-NMR and IR, this product was identified as 1,2-diphenyl-2-mercaptoethylamine hydrochloride containing small amounts of the starting materials and dimethyl formamide.

EXAMPLE 12

The same reactor as described in Example 1 was charged with 15.0 g (0.055 mole) of 4,5-diphenyl-2-mercaptothiazoline, 13.4 g (0.05 mole) of 1,2-diphenyl-2-chloroethylamine hydrochloride, 1.8 g (0.10 mole) of water and 40 ml of dimethyl formamide, and they were heated at 130° to 135° C. for 10 hours. Thereafter, 22.5 g (1.25 moles) of water was added, and the mixture was heated under reflux for 25 hours. After the reaction, the reaction mixture was worked up in the same way as in Example 9 to give 29.2 g of a viscous pale yellow liquid. By $^1$H-NMR and IR, this product was identified as 1,2-diphenyl-2-mercaptoethylamine hydrochloride containing small amounts of the starting materials and dimethyl formamide.

EXAMPLE 13

The same reactor as described in Example 1 was charged with 3.68 g (0.025 mole) of 4,4-dimethyl-2-mercaptothiazoline, 3.6 g (0.025 mole) of 1,1-dimethyl-2-chloroethylamine hydrochloride, 10 g (0.56 mole) of water and 40 ml of 1-butanol, and they were heated at 105° to 110° C. for 50 hours. After the reaction, the reaction mixture was worked up in the same way as in Example 11 to give 7.4 g of a viscous pale yellow liquid. By $^1$H-NMR and IR, this product was determined to be 1,1-dimethyl-2-mercaptoethylamine hydrochloride containing small amounts of the starting materials and 1-butanol. Recrystallization from isopropanol gave 5.1 g of 1,1-dimethyl-2-mercaptoethylamine hydrochloride as white crystals having a melting point of 180° to 182° C.

EXAMPLE 14

The same reactor as described in Example 1 was charged with 17.6 g (0.120 mole) of 4,4-dimethyl-2-mercaptothiazoline, 14.4 g (0.100 mole) of 1,1-dimethyl-2-chloroethylamine hydrochloride, 5.4 g (0.30 mole) of water and 50 ml of 1-butanol, and they were heated at 105° to 110° C. for 15 hours. Then, 40 g (2.22 moles) of water was additionally supplied, and the mixture was heated under reflux for 40 hours. After the reaction, the reaction mixture was worked up in the same way as in Example 11 to give 32.9 g of a viscous pale yellow liquid. By $^1$H-NMR and IR, this product was determined to be 1,1-dimethyl-2-mercaptoethylamine hydrochloride containing small amounts of the starting materials and 1-butanol. Recrystallization from isopropanol gave 22.8 g of 1,1-dimethyl-2-mercaptoethylamine hydrochloride as white crystals having a melting point of 181° to 182.5° C.

EXAMPLE 15

The same reactor as described in Example 1 was charged with 4.7 g (0.026 mole) of 4,4-bis(hydroxymethyl)-2-mercaptothiazoline, 4.4 g (0.025 mole) of 1,1-bis(hydroxymethyl)-2-chloroethylamine hydrochloride, 10 g (0.56 mole) of water and 40 ml of dimethyl formamide, and they were heated at 105° to 110° C. for 50 hours. After the reaction, the reaction mixture was worked up in the same way as in Example 11 to give 9.3 g of a viscous pale yellow liquid. By $^1$H-NMR and IR, this product was determined to be 1,1-bis(hydroxymethyl)-2-mercaptoethylamine hydrochloride.

EXAMPLE 16

The same reactor as described in Example 1 was charged with 18.8 g (0.105 mole) of 4,4-bis(hydroxymethyl)-2-mercaptothiazoline, 17.6 g (0.100 mole) of 1,1-bis(hydroxymethyl)-2-chloroethylamine hydrochloride, 9 g (0.50 mole) of water and 30 ml of dimethyl formamide, and they were heated at 105° to 110° C. for 15 hours. Then. 70 g (3.89 moles) of water was added, and the mixture was heated under reflux for 30 hours. After the reaction, the reaction mixture was worked up in the same way as above to give 37.1 g of a viscous pale yellow liquid. By $^1$H-NMR and IR, this product was determined to be 1,1-bis(hydroxymethyl)-2-mercaptoethylamine hydrochloride containing small amounts of the starting materials and dimethyl formamide.

EXAMPLE 17

The same reactor as described in Example 1 was charged with 7.0 g (0.028 mole) of 4-n-butyl-5-phenyl-2-mercaptothiazoline, 6.2 g (0.025 mole) of 1-n-butyl-2-phenyl-2-chloroethylamine hydrochloride, 10 g (0.56 mole) of water, 10 g (0.36 mole as water) of conc. hydrochloric acid and 30 ml of dimethyl formamide, and they are heated at 105° to 110° C. for 50 hours. The reaction mixture was worked up in the same way as in Example 11 to give 13.7 g of a viscous pale yellow liquid. By $^1$H-NMR and IR, this product was determined to be 1-n-butyl-2-phenyl-2-mercaptoethylamine hydrochloride containing small amounts of the starting materials and dimethyl formamide.

EXAMPLE 18

The same reactor as described in Example 1 was charged with 13.8 g (0.055 mole) of 4-n-butyl-5-phenyl-2-mercaptothiazoline, 12.4 g (0.05 mole) of 1-n-butyl-2-phenyl-2-chloroethylamine hydrochloride, 5 g (0.21 mole as water) of 25% hydrochloric acid and 30 ml of dimethyl formamide, and they were heated at 105° to 110° C. for 15 hours. Then, 50 g (2.08 moles as water) of 25% hydrochloric acid was added, and under reflux, the mixture was heated for 25 hours. After the reaction, the reaction mixture was worked up in the same way as in Example 11 to give 26.9 g of a viscous pale yellow liquid. By $^1$H-NMR and IR, this product was determined to be 1-n-butyl-2-phenyl-2-mercaptoethylamine hydrochloride containing small amounts of the materials and dimethyl formamide.

EXAMPLE 19

The same reactor as described in Example 1 was charged with 4.0 g (0.027 mole) of 5-ethyl-2-mercaptothiazoline, 3.6 g (0.025 mole) of 2-chlorobutylamine hydrochloride, 10 g (0.56 mole) of water, 10 g (0.36 mole as water) of conc. hydrochloric acid and 30 ml of 1-butanol, and they were heated at 105° to 110° C. for 40 hours. After the reaction, the reaction mixture was concentrated to give 7.7 g of a viscous pale yellow liquid. By $^1$H-NMR and IR, this product was determined to be 2-mercaptobutylamine hydrochloride containing small amounts of the starting materials and 1-butanol.

EXAMPLE 20

The same reactor as described in Example 1 was charged with 16.2 g (0.11 mole) of 5-ethyl-2-mercaptothiazoline, 14.3 g (0.10 mole) of 2-chlorobutylamine hydrochloride, 20 g (0.78 mole as water) of 30% hydrochloric acid and 20 ml of 1-butanol, and they were heated at 105° to 110° C. for 15 hours. Then, 50 g (1.94 moles as water) of 30% hydrochloric acid was added, and the mixture was heated under reflux for 30 hours. After the reaction, the reaction mixture was concentrated to give 30.6 g of a viscous pale yellow liquid. By $^1$H-NMR and IR, this product was determined to be 2-mercaptobutylamine hydrochloride containing small amounts of the starting materials and 1-butanol.

EXAMPLE 21

The same reactor as described in Example 1 was charged with 28 g (0.21 mole) of 5-methyl-2-mercaptothiazoline, 26 g (0.20 mole) of 2-chloropropylamine hydrochloride and 56 g (2.8 moles as water) of 10% hydrochloric acid, and they were heated at 100° to 105° C. for 15 hours. Analysis by TLC showed that the 2-chloropropylamine hydrochloride disappeared almost completely, and S,S'-bis(1-methyl-2-aminoethyl)dithiocarbonate was formed as a main product. Heating was continued, and the reaction was carried out further for 40 hours. After the reaction, the reaction mixture was worked up in the same way as in Example 7 to give 42.9 g of white crystals. By iodometric analysis, these crystals were found to have a purity of 99.0% as 2-mercaptopropylamine hydrochloride. The melting point of the crystals was 91° to 92° C.

EXAMPLE 22

The same reactor as described in Example 1 was charged with 19.6 g (0.165 mole) of 2-mercaptothiazoline, 17.4 g (0.150 mole) of 2-chloroethylamine hydrochloride and 15 g (0.67 mole as water) of 20% hydrochloric acid, and they were heated at 110° C. for 10 hours. Analysis by TLC showed that the 2-chloroethylamine hydrochloride disappeared almost completely. The reaction mixture was cooled to room temperature, and 80 ml of chloroform was added to remove the unreacted 2-mercaptothiazoline by extraction. The residue was concentrated to dryness, and recrystallized from isopropanol to give 34.1 g of white crystals. By $^1$H-NMR and IR, the crystals were determined to be S,S'-bis(2-aminoethyl)dithiocarbonate hydrochloride.

Thirty grams (0.119 mole) of the resulting white crystals and 60 g (2.67 moles as water) of 20% hydrochloric acid were put in a glass pressure vessel, and heated at 130° C. and 5 to 8 kg/cm$^2$ for 15 hours. After the reaction the reaction mixture was concentrated to dryness under reduced pressure to give 26.9 g of white crystals. By iodometric analysis, the crystals had a purity of 99.1% as 2-mercaptoethylamine hydrochloride.

What we claim is:

1. A process for producing 2-mercaptoethylamine hydrohalides of the general formula

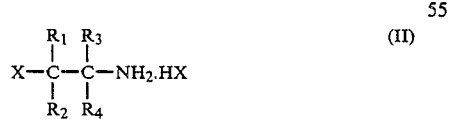

wherein $R_1$, $R_2$, $R_3$ and $R_4$ are identical or different, and each represents a hydrogen atom, a lower alkyl group, a hydroxy-substituted lower alkyl group or a phenyl group, and X represents a halogen atom, which comprises reacting 2-mercaptothiazoline of the general formula

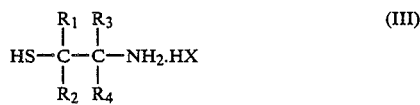

wherein $R_1$, $R_2$, $R_3$ and $R_4$ are as defined above, with a 2-halogenoethylamine hydrohalide of the general formula

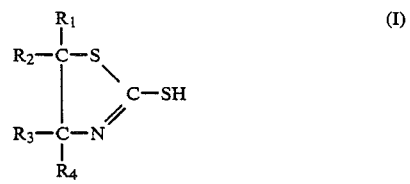

wherein $R_1$, $R_2$, $R_3$, $R_4$ and X are as defined above, in an aqueous solvent.

2. The process of claim 1 wherein the 2-mercaptothiazoline is 2-mercaptothiazoline, 5-methyl-2-mercaptothiazoline, 4,4-dimethyl-2-mercaptothiazoline, 4,5-diphenyl-2-mercaptothiazoline, 4,4-bis(hydroxymethyl)-2-mercaptothiazoline, 4-n-butyl-5-phenyl-2-mercaptothiazoline or 5-ethyl-2-mercaptothiazoline.

3. The process of claim 1 wherein the 2-halogenoethylamine hydrohalide is a hydrohalide of 2-chloroethylamine, 2-bromoethylamine, 1-methyl-2-chloroethylamine, 1-methyl-2-bromoethylamine, 1,2-diphenylchloroethylamine, 1,1-bis(hydroxymethyl)-2-chloroethylamine, 1-n-butyl-2-phenyl-2-chloroethylamine or 2-chlorobutylamine.

4. The process of claim 1 wherein the reaction is carried out at a temperature in the range of 20° C. to 200° C.

5. The process of claim 1 wherein the reaction is carried out in the further presence of an organic solvent inert to the reaction.

6. A process for producing 2-mercaptoethylamine hydrohalides of the general formula

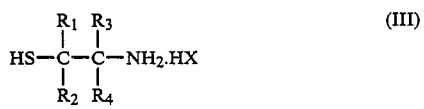

wherein $R_1$, $R_2$, $R_3$ and $R_4$ are identical or different and each represents a hydrogen atom, a lower alkyl group, a hydroxy-substituted lower alkyl group or a phenyl group, and X represents a halogen atom, which comprises reacting a 2-mercaptothiazoline of the general formula

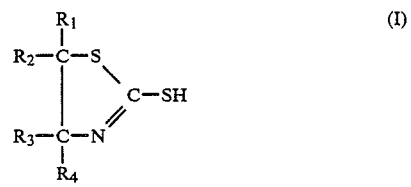

wherein $R_1$, $R_2$, $R_3$ and $R_4$ are as defined above, with a 2-halogenoethylamine hydrohalide of the general formula

wherein $R_1$, $R_2$, $R_3$, $R_4$ and X are as defined above, in less than 20 moles, per mole of the compound of general formula (II), of water to form an S.S'-bis(2-aminoethyl)dithiocarbonate derivative of the general formula

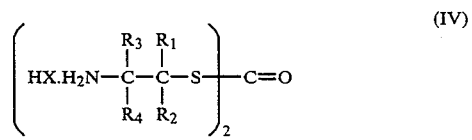

wherein $R_1$, $R_2$, $R_3$, $R_4$ and X are as defined above, and hydrolyzing the resulting compound of general formula (IV).

7. The process of claim 6 wherein the 2-mercaptothiazoline is 2-mercaptothiazoline, 5-methyl-2-mercaptothiazoline, 4,4-dimethyl-2-mercaptothiazoline, 4,5-diphenyl-2-mercaptothiazoline, 4,4-bis(hydroxymethyl)-2-mercaptothiazoline, 4-n-butyl-5-phenyl-2-mercaptothiazoline, or 5-ethyl-2-mercaptothiazoline.

8. The process of claim 6 wherein the 2-halogenoethylamine hydrohalide is a hydrohalide of 2-chloroethylamine, 2-bromoethylamine, 1-methyl-2-chloroethylamine, 1-methyl-2-bromoethylamine, 1,2-diphenylchloroethylamine, 1,1-bis(hydroxymethyl)-2-chloroethylamine, 1-n-butyl-2-phenyl-2-chloroethylamine or 2-chlorobutylamine.

9. The process of claim 6 wherein the reaction is carried out at a temperature of 20° C. to 200° C.

10. The process of claim 6 wherein the reaction is carried out in the further presence of an organic solvent inert to the reaction.

11. The process of claim 6 wherein the hydrolysis is carried out at a temperature in the range of 20° C. to 200° C.

12. The process of claim 1 or 6 wherein said aqueous solvent is an aqueous solution of a hydrohalic acid.

13. The process of claim 1 or 6 wherein the amount of the 2-mercaptothiazoline is 1.02 to 1.20 moles per mole of the 2-halogenoethylamine hydrohalide.

14. The process of claim 1 wherein the aqueous solvent comprises water in an amount of at least 20 moles of water per mole of the 2-halogenoethylamine hydrohalide or 2-mercaptothiazoline reactant.

15. The process of claim 6 wherein the aqueous solvent comprises water in an amount of 1.5 moles to 15 moles of water per mole of the 2-halogenoethylamine hydrohalide or 2-mercaptothiazoline reactant.

16. A process for producing 2-mercaptoethylamine hydrohalides of the general formula

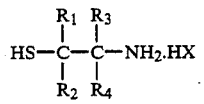

wherein $R_1$, $R_2$, $R_3$ and $R_4$ are identical or different, and each represents a hydrogen atom, a lower alkyl group, a hydroxy-substituted lower alkyl group or a phenyl group, and X represents a halogen atom, which comprises reacting a 2-mercaptothiazoline of the general formula

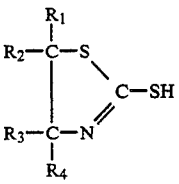

wherein $R_1$, $R_2$, $R_3$ and $R_4$ are as defined above, with a 2-halogenoethylamine hydrohalide of the general formula

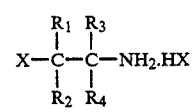

wherein $R_1$, $R_2$, $R_3$, $R_4$ and X are as defined above, in at least 1.5 moles of water per mole of the 2-halogenoethylamine hydrohalide or the 2-mercaptothiazoline reactant.

17. The process of claim 16 wherein the amount of water is less than 20 moles per mole of the 2-halogenoethylamine hydrohalide or the 2-mercaptothiazoline reactant to form an S,S'-bis(2-aminoethyl)dithiocarbonate derivative of the general formula

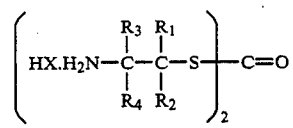

wherein $R_1$, $R_2$, $R_3$, $R_4$ and X are as defined above, and the resulting compound of general formula (IV) is hydrolyzed to form the 2-mercaptoethylamine hydrohalide.

18. The process of claim 16 or 17 wherein the reactants are reacted under acidic conditions.

* * * * *